(12) United States Patent
Frey et al.

(10) Patent No.: US 7,431,685 B2
(45) Date of Patent: Oct. 7, 2008

(54) METHOD AND DEVICE FOR INVESTIGATING SUBSTANCE LIBRARIES

(75) Inventors: Andreas Frey, Gross Niendorf (DE); Juergen Helfman, Kleinmachnow (DE); Marcus Alexander Schmidt, Havixbeck (DE); Gerhard Mueller, Berlin (DE)

(73) Assignee: Laser- und Medizin Technologie GmbH, Berlin (DE)

( * ) Notice: Subject to any disclaimer, the term of this patent is extended or adjusted under 35 U.S.C. 154(b) by 655 days.

(21) Appl. No.: 10/239,986

(22) PCT Filed: Mar. 28, 2001

(86) PCT No.: PCT/EP01/03530

§ 371 (c)(1),
(2), (4) Date: Feb. 19, 2003

(87) PCT Pub. No.: WO01/72412

PCT Pub. Date: Oct. 4, 2001

(65) Prior Publication Data

US 2003/0165998 A1 Sep. 4, 2003

(30) Foreign Application Priority Data

Mar. 28, 2000 (DE) ................. 100 15 391
Mar. 28, 2000 (DE) ............... 200 05 738 U

(51) Int. Cl.
*C40B 50/00* (2006.01)

(52) U.S. Cl. ............... 506/23; 435/6; 435/68.1; 536/25.3

(58) Field of Classification Search ........ 435/4, 435/7.1, 287.3, 287.9, 288.2, 288.3, DIG. 46, 435/DIG. 49
See application file for complete search history.

(56) References Cited

U.S. PATENT DOCUMENTS

| 5,368,823 | A | | 11/1994 | McGraw | |
|---|---|---|---|---|---|
| 5,472,672 | A | * | 12/1995 | Brennan | ............... 422/131 |
| 5,759,779 | A | | 6/1998 | Dehlinger | |
| 5,763,263 | A | | 6/1998 | Dehlinger | |
| 5,798,035 | A | | 8/1998 | Kirk | |
| 5,831,070 | A | * | 11/1998 | Pease et al. | .............. 536/25.3 |
| 5,843,767 | A | | 12/1998 | Beattie | |
| 6,716,629 | B2 | * | 4/2004 | Hess et al. | ............... 435/420 |
| 2001/0029028 | A1 | * | 10/2001 | Foote | ............... 435/7.1 |

FOREIGN PATENT DOCUMENTS

WO    WO 00/66259 A1    11/2000

OTHER PUBLICATIONS

Ronald Frank, "Spot-Synthesis: An Easy Technique for the Positionally Addressable, Parallel Chemical Synthesis on a Membrane Support," vol. 48 ( No. 42), p. 9217-9232, ( 1992).

* cited by examiner

*Primary Examiner*—J D Schultz
*Assistant Examiner*—Jeffrey S. Lundgren
(74) *Attorney, Agent, or Firm*—Hahn Loeser & Parks LLP; John J. Cunniff

(57) ABSTRACT

The aim of the invention is to investigate the bonding of substances to target molecules. This is achieved by means of a densely packed device wherein various target molecules are bonded in a large number of sample areas. Cross-contamination and evaporation need to be minimized. The active surface of the sample areas have to be maximized. The inventive solution resides in the use of carrier plates, containing densely packed capillary structures and having a very large inner surface despite small outer dimensions. 1000 times more molecules can be bonded than on a flat outer surface of a comparable size. Cross contamination is avoided by the lack of cross links between the capillaries. Evaporation is minimized by a small outer surface. After the inner surface of the capillaries has been silanized, peptides and peptidomimetics are synthesized in a locally targeted manner. The molecular interactions of components of the substance library with active substances in a solution or a suspension are investigated by means of a local resolution optical detection method. Handling, especially cleaning and covering with substances, is carried out in a simple manner by rinsing liquids through the capillary plate.

7 Claims, 4 Drawing Sheets

METHOD AND DEVICE FOR INVESTIGATING SUBSTANCE LIBRARIES

BACKGROUND ART

In contrast to solid-phase immobilised miniaturised nucleic acid libraries, about which there are a large number of publications in technical journals and patents (S. P. A. Fodor et al. (1991), Light-directed, spatially addressable parallel chemical synthesis. science 251.767-773; E. M. Southern et al. (1992), Analyzing and comparing nucleic acid sequences by hybridization to arrays of oligonucleotides: evaluation using experimental models. Genomics 13:1008-1017; G. McGall. et al. (1996), Light-directed synthesis of high-density oligonucleotide arrays using semiconductor photoresists, Proc. Natl. Acad. Sci. USA 26:13S55-13560, M. Chee et al. (1996), Accessing genetic information with high density DNA arrays. Science 274:610-614; 5. Singh-Gasson et al. (1999), Maskiess fabrication of light-directed oligonucleotide microarrays using a digital micromirror array. Nat. Biotechnol. 17:974-978; S. P. A. Fodor et al. (1995), Arrays of materials attached to a substrate. U.S. Pat. No. 5,744,305; S. P. A. Fodor et at. (1995), Very large scale immobilised polymer synthesis. U.S. Pat. No. 5,424,186; G. H. McGall et al. (1995), Spatially-addressable immobilization of oligonucleotides and other biological polymers on surfaces. U.S. Pat. No. 5,412,087, A. S. Heuermann (1999), Method and device for photolithographic production of DNA, PNA and protein chips. WO 9960156A2, G. H. McGall und N. Q. Nam (2000), Synthesis of oligonucleotide arrays using photocleavableprotecting groups. U.S. Pat. No. 6,022,963) solid-phase immobilised greatly miniaturised peptide or peptidomimetic libraries have hitherto been described only in a small number of works (S. P. A. Fodor et al. (1991), light-directed, spatially addressable parallel chemical synthesis. Science 25 1:767-773; C. P. Holmes et al. (1995), The use of light-directed combinatorial peptide synthesis in epitope mapping. Biopolymers 37:199-211; M. C. Pirrung et al. (1992), Large scale photolithographic solid phase synthesis of polypeptides and receptor binding thereof U.S. Pat. No. 5,143,854, M. C. Pirrung et al. (1995), Large scale photolithographic solid phase synthesis of an array of polymers. U.S. Pat. No. 5,405,783).

One of the main reasons why miniaturised peptide libraries, so-called 'peptide chips', have hitherto not yet achieved widespread dissemination, is the relatively high level of expenditure involved in the production of such arrangements if the conventional photolithographic synthesis methods used in relation to 'DNA chips' on planar supports are used. In the case of nucleic acids, those methods make use of the fact that there are only four different naturally occurring nucleotides (deoxyadenosine, deoxycytidine, deoxyguanosine and thymidine) for producing the deoxyribonucleic acid oligomers, that the coupling times when forming the oligonucleotides are relatively short (less than 30 minutes) and the yields of the individual coupling steps are very good (more than 99%). All three criteria have a crucial influence on the production time for such chips and thus the economy of the entire process.

In the photolithographic synthesis of oligonucleotides, firstly a support which is completely protected with a photolabile protective group is cleared of protection in positionally directed fashion by irradiation with light at the locations at which for example a thymidine phosphate is to be applied, and then the entire support is incubated with thymidinephosphoamidite which is photolabily protected at the 5'-OH and suitable coupling reagents. Coupling is thus effected only at the desired locations and the entire procedure has to be repeated for the other three nucleotides before the first dinucleotide can be synthesised. In the case of a chip which is occupied with 20-mer oligonucleotides 80 coupling, washing and protection-removal cycles are therefore required.

In the case of a peptide however the number of components which can be used for coupling is markedly higher than in the case of the nucleic acids. There are 20 proteinogenic amino acids, some naturally occurring non-proteinogenic amino acids (for example ornithine), the same number of corresponding D-amino acids and a continuously rising number of artificial amino acids such as for example cyclohexylalanine, aminoisobutyric acid, Norvaline, etc, also each in D-and L-form. In summary it can be assumed that at the present time about 100 different amino acids are available for the chemical synthethis of peptides and peptidomimetics. If—considered conservatively—only half of those reagents are used for the synthethis of a substance library, that gives 1000 coupling and protection-removal cycles in the synthesis of a 20-mer peptide or peptidomimetic library. In addition solid-phase peptide synthesis generally affords coupling yields of 85-90% with reaction times of about 30 minutes so that usually at least one repetition of the coupling step with fresh reagents is necessary to achieve the required synthesis yields. This means that extremely long synthesis times of weeks up to several months have to be calculated into the procedure for the production of a peptide or peptidomimetic library immobilised on a two-dimensional support if operation is implemented using photolithographic methods. Consequently hitherto only photolithographic syntheses of short peptides of low sequence variability have been described (S P A Fodor et al (1991) Light-directed, spatially addressable parallel chemical synthesis, Science 251; 767-773, C P Holmes et al (1995), The use of light directed combinatorial peptide synthesis in epitope mapping. biopolymers 37:199-211; M C Pirrung et al (1992), Large scale photolithographic solid phase synthesis of polypeptides and receptor binding thereof U.S. Pat. No. 5,143,854).

An alternative method which considerably reduces the number of working steps is based on the simultaneous protection removal of all support-bonded reaction partners followed by parallel or sequential positionally directed application of the different amino acid reaction mixtures into defined sample areas. In that way it is also possible to synthesise libraries from longer and complex peptides or peptidomimetics in an acceptable time frame. The main problem in this respect however is the cross-contamination which is to be expected of the reactants if the sample areas are close together. Dense packing of the sample areas in turn is desirable in order sufficiently to miniaturise the substance library.

One possible way of resolving the problem involves increasing the surface tension in the regions between the sample areas of the planar support so that the reaction mixtures remain in the form of small droplets in the region of the sample areas. To achieve that aim the support surface must be fluoroalkylated between the sample areas, as described in T M Brennan (1995) Method and apparatus for conducting an array of chemical reactions on a support surface, U.S. Pat. No. 5,474,796; T M Brennan (1997), Method and apparatus for conducting an array of chemical reactions on a support surface, EP 703 825B1 and T M Brennan (1999), Method and apparatus for conducting an array of chemical reactions on a support surface, U.S. Pat. No. 5,985,551. The method however suffers from the disadvantage that without a protective enclosure the drops are severely subjected to evaporation, which can represent a major problem particularly when dealing with very small sample volumes.

An alternative way of resolving the cross-contamination problem lies in the use of a porous membrane which immediately sucks up the amino acid reaction mixture at the location of application (R Frank (1992), Spot synthesis: an easy technique for the positionally addressable, parallel chemical synthesis on a membrane support, Tetra hedron 48:92 17-9232; R Frank and S Güler (1992), Verfahren zur schnellen Synthese von trägergebundenen oder freien Peptiden oder Oligonukleotiden, damit hergestelltes Flachmaterial, Verwendung sowie Vorrichtung zur Durchführung des Verfahrens, [Method of fast synthesis of support-bonded or free peptides or oligonucleotides, flat material produced therewith, use and apparatus for carrying out the method], WO 92/04366; J Schneider-Mergener (1994), Verfahren zur Synthese und Selektionierung von Sequenzen aus kovalent verbundenen Bausteinen, [Method of synthesising and selecting sequences of covalently joined components], WO 94/20521). The unordered capillaries in the porous membrane, with increasing miniaturisation of the sample areas, result however in cross-contamination and the relatively large surface area of the membrane also results in this method in evaporation of the solvent and thus under some circumstances in an adverse influence on the coupling reaction. A further problem which occurs when using the cellulose membranes usually employed here is in part very great heterogeneity of the synthesised product. In a mass-spectroscopic investigation of the entire material detached from a sample area, both amino-terminally and also carboxy-terminally shortened peptides are found, which occur due to the fact that the synthesis breaks down too early for steric reasons within the membrane and chain re-starts can still take place by virtue of esterification of amino acids directly at the cellulose substrate even in later synthesis cycles. In particular peptides which have been carboxy-terminally shortened by 1-4 amino acids are demonstrated (D Goehmann and A Frey, unpublished results). Complete blocking of the hydroxyl groups of the cellulose by acetylation or similar measures for preventing chain re-starts is prohibited as in that way the support achieves a higher degree of solubility in the solvents usually employed for solid-phase peptide synthesis and loses a considerable amount of mechanical stability (D Goehmann and A Frey, unpublished results). A further disadvantage in the use of membranes lies in their optical properties. In particular cellulose membranes have strong inherent fluorescence in the emission range of many commercially available fluorophores so that the sensitivity of identification of active substances which bind to the target molecules is greatly reduced (J Helfmann, unpublished results).

A further approach for resolving the problem of cross-contamination in charging a planar support with a substance library involves using a microreactor system in which the planar support represents a vessel wall for a plurality of reaction cavities and at the same time the support medium for the target molecules. The reaction cavities which are enclosed on all sides in that way are specifically supplied with the desired reagents and washing solutions for example by changing the positioning of the microreactor block or by means of micropassages, electro-osmotic pumps and microvalves in the reactor block. Waste products are removed in a similar manner (J L Winkler et al (1995), Very large scale immobilised polymer synthesis using 10 mechanically directed flow paths, U.S. Pat. No. 5,384,261; P J Zanzucchi et al (1997), Method of synthesis of a plurality of compounds in parallel using a partitioned solid support, U.S. Pat. No. 5,643,738; P J Zanzucchi et al (1998), Partitioned microelectronic device array, U.S. Pat. No. 5,755,942; S C Cherukuri et al (1999), Method and system for inhibiting cross-contamination in fluids of combinatorial chemistry device, U.S. Pat. No. 5,980,704). A crucial disadvantage of such arrangements however is their susceptibility to particulate impurities in the reaction solutions, in particular if the passages are only a few micrometers in diameter and the direction of flow of the reagents and waste products in the microreactor block is changed a plurality of times. The risk of blockage of the microreactor system is very great in particular in the case of coupling reactions with carbodiimides as the organic urea derivatives which are produced in this case have a strong tendency to crystallisation. In the worst case then the complete microreactor block has to be replaced.

The existing methods and methods described in the literature or patents all have serious disadvantages. Either there is not a large surface area and thus not a high level of detection sensitivity with small external dimensions, or the synthesis times are overall excessively long. Optical detection is severely interfered with due to inherent fluorescence and chain breakages result in a non-homogenous sample. When dense packing of the substance library is involved cross-contamination between various sample areas is to be observed. When dealing with small volumes evaporation influences the results. Handling is complicated or very sensitive in relation to particles.

SUMMARY OF THE INVENTION

The detection sensitivity for the interaction (for example binding) of active substances in the liquid phase with solid-phase bonded target molecules is substantially determined by the number of solid-phase bonded target molecules. In the case of an ideally planar support the solid phase available for binding is limited to the external surface of the support. An optical detection system (for example fluorescence detection) is however always capable of additionally detecting a given volume above and below the external surface.

The subject-matter of the invention is an arrangement and a method as defined in the claims. Particular configurations of the invention are claimed in the appendant claims and set forth in the description hereinafter without the invention being restricted to the illustrated embodiments.

The invention generally concerns an arrangement for receiving and building up a substance library and a method of producing such a library. In that respect the term 'substance library' is used to denote a library or collection of many different but usually similar substances in the same class. The library usually serves to search through the substances belonging thereto on the basis of some property and to find and possibly select therein suitable members or target substances. Examples of substances which can form a substance library according to the invention and which are also referred to as target molecules are inter alia DNA sequences, peptides, polypeptides and peptoid substances.

In particular the invention concerns a structure which can comprise glass, quartz, ceramic, plastic material, semi-metal or metal and which by virtue of a high density of small capillaries 1 (diameters 5-100 μm) has a large internal surface area with a multiple of the external surface area (see FIG. 1). The overall thickness of the capillary plate 4 (thickness up to 10 mm) and thus the total length of the capillaries 1 and the surface thereof is detected by a detection apparatus. As the maximum occupation (number of molecules) of the capillary plate 4 is determined by the size of the internal surface area, and that is larger by a multiple (between 100 and 1000 times) in comparison with the external surface area, the detection sensitivity is increased to the same degree when using the capillary plate 4, in comparison with a planar sample arrangement.

Surprisingly it has been found that peptide and peptoid molecules can be synthesised on a silanised surface of high quality and the number of chain re-starts can be almost completely eliminated. If in addition a prolonged anchor molecule which serves as a spacer is also coupled between the surface and the target molecule, the chain breakages are greatly reduced and accessibility for the active substances is considerably improved.

To produce a library of target molecules, from which each individual species or defined mixtures of given species must be synthesised or bonded to previously defined regions of the capillary plate 4, firstly the internal surface of the capillary plate 4 must be enabled for covalent bonding of the target molecules. That is effected by applying an organosilane layer which has functional groups for anchoring peptidic or peptoid target molecules. Preferably a γ-aminopropyltrialkoxysilane is used for that purpose, however other organofunctional silanes such as for example γ-mercaptopropyltrialkoxysilane are also suitable for that purpose. When using metal or semimetal capillary plates an oxide layer must be produced first for binding the silane by means of surface oxidation of the capillary plate.

Then, a respective sample area 3 is applied to that organofunctionalised capillary plate 4 by position-dependent application of a substance (for example by pipetting). In the simplest case the substance can be a reagent which temporarily protects the functional groups of the organosilane layer intended for binding. In a preferred embodiment however an anchor molecule is applied in the sample areas 3, with which the target molecules can be pushed between 0.5 and 20 nm beyond the internal surface of the capillary plate 4 in order in that way to permit better active substance binding. The anchor reagent used is for example fluorenylmethoxycarbonyl (FMOC)-protected α-amino-poly(ethyleneglycol)-ω-propionic acid-N-hydroxybenzotriazole ester.

Then, all regions of the capillary plate 4 which are not derivatised with protection or anchor reagents are chemically so saturated that neither synthesis or coupling of target molecules nor non-specific binding of active substances can occur there at a later time. Chemical saturation of the non-sample areas can be effected depending on the respective requirements involved with hydrophilic, hydrophobic or oleophobic groups. Saturation is effected with acetyl residues under standard conditions.

In the following steps for production according to the invention of a substance library which is also composed of a plurality of sample areas each with a respective species of target molecules, the protective group on the support or the anchor molecules is synchronously removed in all sample areas 3 and then coupling or synthesis of the peptidic and peptoid target molecules is effected in the sample areas 3 provided for same.

Knowledge of the substance which is bonded or synthesised at each location in that way permits parallel analysis of the interactions of various target molecules with applied active substances. A prerequisite in that respect is that no mutual contamination occurs in the operation of position-dependently applying or synthesising the target molecules.

In a development of the concept of the invention, that is achieved by the parallel arrangement of the capillaries 11 which extend perpendicularly to the plate surface and which are only open towards the external plate surfaces. The absence, which is achieved in that way, of any cross-connections between various sample areas 3 successfully prevents cross-contamination phenomena, even when the sample areas 3 involve a high level of density. A sample area 3 includes a plurality of (for example up to 4000) capillaries 1. Substances which are applied thereto by pipetting are drawn into the capillaries 1, which can also be assisted depending on a respective liquid involved by the production of a reduced pressure on a capillary plate side. Flow out of the capillaries 1 by way of a plurality of capillaries 1 into another sample area 3 is out of the question as the liquid is held in the capillary by capillary force. With these liquids, solutions are effectively prevented from dripping out of the capillaries 1, due to the very low viscosity involved, by a plate 12 (FIG. 2) with a hydro- and oleophobic surface, which is positioned to the underside of the capillary plate 4.

In a further development of the concept of the invention, by virtue of the capillaries 1 which are open towards both external plate surfaces, simple automation of a solid-phase peptide synthesis procedure which is implemented in the capillary plate 4 is also possible. In that respect, after the conclusion of a coupling step the reagents and waste products can be sucked out of the capillaries 1 unidirectionally by applying vacuum to the underside of the capillary plate 4 and the capillaries 1 are synchronously flushed by applying washing solutions on the top side of the capillary plate 4. For prolonged incubation procedures and washing steps, all reagents and washing solutions which are to be synchronously applied to all regions of the capillary plate 4 can also be brought into contact with all capillaries 1 by flooding the entire capillary plate 4 from the underside, and then removed again by applying reduced pressure. An apparatus for the synchronous application of washing and reagent solutions to all regions of the capillary plate 4 is shown in FIG. 2.

After different target molecules have been synthesised or bonded on the target areas 3 in position-dependent fashion in that way, the entire support is exposed to a dissolved or suspended particulate active substance in the liquid phase, in which respect it is necessary to ensure that, when using suspensions, the particle size is always markedly below the inside diameter of the capillaries 1. The redundancy with many capillaries per sample area however means that individual particles do not represent a risk of blockage for an entire sample area. Incubation of the substance library with active substance solutions or suspensions and flushing operations before and after same are carried out in a preferred embodiment involving a simple structure, as is shown in FIG. 3.

Analysis of active substance binding is effected in a preferred embodiment optically by means of fluorescence markings by binding a fluorophore to the active substances. In an alternative embodiment the fluorophores are bonded to the target molecules. For reading-out purposes, the individual sample volume which is composed of the thickness of the capillary plate and the sample region 3 is completely penetrated by excitation light and also completely detected by the detection optics. The plurality of sample locations is detected by time-sequential rastering, in which case either the capillary plate is moved two-dimensionally under the stationary optical arrangement or the beam path is moved over the capillary plate. In accordance with the invention the use of quartz or glass as the material for the capillary plate here minimises the influence of Detailed Description of the Solution According to the Invention in a Preferred Embodiment The way in which the entire capillary plate is pre-treated is now described. The sample areas are then produced and the substances synthesised thereon. An automatic device is described for all procedures to which the capillary plate is completely exposed, such as for example washing. That device is combined with a pipetting robot so that the capillary plate can be washed and protection removed therefrom in the same device, and the individual synthesis steps can be implemented therein. A further device is described for investigating the binding of an active substance to the substance library, the capillary plate being fitted into the further device and brought into contact with the active substance. Optical detection of the binding effect is carried out at the same time herein.

Derivatisation of the Capillary Plate for Receiving the Substance Library

The capillary plate is produced by etching from homogeneous glass, in an alternative method from heterogeneous glass. Oxidation of silicon and metal surfaces and silanisation of glass, quartz, silicon, ceramic and oxidised silicon or metal surfaces is state of the art and has already been described many times in the specialist and patent literature (for example regarding the surface oxidation of a silicon support: A W Flounders et al (1997), Patterning of immobilised antibody layers via photolithography and oxygen plasma exposure, Biosensors Bioelectronics 12:447-456; for example regarding silanisation: M Lynn (1975), Inorganic support intermediates: covalent coupling of enzymes on inorganic supports, In: 'Immobilised Enzymes, Antigens, Antibodies and Peptides', H H Weetall, Hrsg, Marcel Dekker, New York, N.Y., USA, pages 1-48; H M Weetall (1976), Covalent coupling methods for inorganic support materials, Methods Enzymol 44:134-148).

In the preferred embodiment for that purpose an untreated capillary plate 4 with surface oxide, ceramic or glass coating is freed of adsorbed organic compounds either in an oxidising acid such as for example chromosulfuric acid or hot concentrated nitric acid, for one hour, washed between five and ten times by sucking through high-purity water (on a suction filter or a Büchner funnel, glass frit or a rinsing device developed especially for the capillary plate 4 (FIG. 2)), and dried at 250° C.

Alternatively adhering organic compounds can be removed by pyrolysis at 500° C. in an oxygen atmosphere. After cooling the capillary plate 4 is coated for 18 hours at ambient temperature in a solution of 2% (v/v) γ-aminopropyltriethoxysilane in water/acetone (1:1), washed ten times by sucking through acetone, left to dry and sintered overnight at 120° C.

Definition of the Sample Areas

In the preferred embodiment definition of the sample areas 3 is a two-stage method, wherein firstly portions of a reaction solution with anchor molecules are pipetted by means of a programmable pipetting robot into given regions of the capillary plate 4 which thus become sample areas 3. In the second step all reactive groups in the non-sample areas are saturated with acetyl residues.

For that purpose in each case between about 0.4 and 4000 ml of a solution which contains a double molar excess—with respect to the number of amino functions in the corresponding region of the derivatised capillary plate 4—of α-FMOC-aminopoly(ethyleneglycol)propionic acid-ω̄-N-hydroxybenzotriazole ester in N-methylpyrolidone, pipetted into the future sample areas 3 of the capillary plate 4, incubated for for example four hours at ambient temperature, in each case washed three times by sucking through dimethylformamide and absolute ethanol, and dried under clean room conditions in an air flow. The entire coupling and washing cycle can be repeated between one and three times to increase the coupling yield. The α-FMOC-aminopoly(ethyleneglycol)propionic acid-ω̄-N-hydroxybenzotriazole ester is immediately previously produced for example by the reaction of α-FMOC-aminopoly(ethyleneglycol)propionic acid with 2-(1H-benzotriazol-1-yl)-1,1,3,3-tetramethyluronium-hexafluoro-phosphate (HBTU) (for example in a ratio of 1:1.2) or in situ by radical ester interchange of for example α-FMOC-aminopoly(ethyleneglycol)propionic acid-ω̄-hydroxysuccinimide ester with water-free N-hydroxybenzotriazole and diisopropylcarbodiimide (in a ratio of 1:0.5:0.5) in N-methylpyrrolidone.

In the subsequent saturation procedure the entire capillary plate 4 is incubated for example in each case three times for one hour in each case at ambient temperature in between five and ten times the internal plate volume of a solution of 2% (v/v) acetic anhydride, and 1% (v/v) diisopropylethylamine in dimethylformamide, wherein the plate is moved in the solution every 15 minutes in such a way that the reaction solution is replaced in the capillaries 1. Thereafter the capillary plate 4 is washed on a frit or suction filter three times in each case with dimethylformamide and ethanol and dried in an air flow.

In the following protection removal procedure the saturated capillary plate 4 is incubated three times in each case for 5 minutes at ambient temperature in between five and ten internal plate volumes of a solution of 20% (v/v) piperidine in dimethylformamide. Thereafter the capillary plate 4 is washed and finally dried as described above.

Production of the Substance Library in the Sample Areas

Synthesis of the substance library of peptidic or peptoid target molecules takes place semi- or fully automatically using the standard FMOC synthesis process for cellulose filter-immobilised peptide libraries (R Frank (1992), Spot synthesis: an easy technique for the positionally addressable, parallel chemical synthesis on a membrane support. Tetrahedron 48:9217-9232), wherein the solutions which contain the activated, amino-terminally and side chain-protected amino acids are pipetted by means of a pipetting robot into the corresponding sample areas 3 of the capillary plate and there drawn by capillary forces into the capillaries 1 and incubated for the course of the coupling reaction. In the fully automatic process (see FIG. 2) the capillary plate 4 is coated with 5 times the internal plate volume of dimethylformamide within 30 seconds and the reaction mixtures sucked away, followed by the washing solution layered thereover, by reduced pressure. Then, either the amino functions which have not reacted are blocked by means of acetic anhydride or after further washing of the capillary plate 4 in dimethylformamide and ethanol the entire coupling cycle is repeated between one and three times before the amino functions which have not reacted are blocked and then the FMOC protection groups are removed in the sample areas 3 of the entire capillary plate 4. That synthesis cycle is repeated until the peptides are obtained in the desired length. Then the side chains of the amino acids have the protection removed therefrom, the entire capillary plate 4 is washed with dimethylformamide and ethanol, dried under clean room conditions in an air flow, welded into a plastic film under protective gas (for example argon or nitrogen) and stored at −70° C. in the presence of drying agent until required for further investigation of the binding of active substances to the substances on the capillary plate.

As an alternative thereto it is also possible to apply to the free amino functions in the sample areas 3 of the capillary plate 4 for example bromoacetyl residues for coupling thiol-bearing peptides or aldehyde residues for binding proteins. Which bioconjugate chemistry is optimally suited here depends on the individual requirements of the peptidic or peptoid target molecules to be coupled and cannot be generally applicably described at this point.

Device for Fully Automatic Washing, Saturation and Protection Removal

Fully automatic washing, saturation and protection removal is the preferred embodiment in terms of producing the substance library. It is preferred over a manual method as it saves on working time and reagents and the entire synthesis procedure is shortened and made more cost-efficient (FIG. 2).

For mounting purposes the capillary plate 4 is fitted on to the underside of a synthesis table 6 which is fixedly connected to a pipetting robot. In this case the edge regions 5 of the capillary plate come to lie on a soft, solvent-resistant seal 7. Spacers 8 are then pushed to close to the edge regions 5 around the capillary plate 4 and secured to prevent them from moving by screwthreaded bolts 9 so that the capillary plate 4 is stationarily positioned on the sample table. Thereafter the upper part of the synthesis table 10 is fitted on to the screwthreaded bolts 9 and pulled by means of a nut 11 against the capillary plate 4 and the spacer 8 or the lower part of the synthesis table 6 so that the seals 7 disposed in the upper and lower parts of the synthesis table 10 and 6 are compressed and seal off the capillary plate 4 towards the side.

For charging the sample areas 3 the hydrophobically and oleophobically coated piston 12 is pushed against the underside of the capillary plate 4 so that no reaction solution can issue downwardly from the capillary plate 4 during the coupling reaction.

For the washing operation after termination of the coupling reaction the entire capillary plate 4 is coated with washing solution from the washing solution feed flow means 13, the piston 12 is moved downwardly and vacuum is applied to remove the solutions sucked through the capillary plate 4 at the discharge 14. The piston 12 is then moved back to the underside of the capillary plate 4 again, the capillary plate 4 is again covered with washing solution and the washing operation is repeated as may be desired (FIG. 2A). After the conclusion of the washing operation air is sucked through the capillary plate 4 until all solvent residues are evaporated. The piston is then moved back to the capillary plate 4 again and a renewed pipetting cycle is carried out, and the plate is saturated or protection removed therefrom. For saturation of unreacted amino functions and for protection removal from amino functions the piston 12 is moved downwardly and the cavity which occurs by virtue of retraction of the piston 12 beneath the capillary plate 14 is filled with the desired reaction solution through the reagent feed flow means 15. When the discharge 14 and the reagent feed flow means 15 are closed the piston is moved slowly up and down for the duration of the reaction so that the reaction solution flows in a uniform flow through the capillaries 1 and the reaction can take place (FIG. 2B). The capillary plate 4 is then washed as described above.

Device for Binding Active Substances to the Substance Library Immobilised on the Capillary Plate Investigation of the binding of active substances to the substance library on the internal surface of the capillary plate 4 requires a device with which an active substance solution or suspension can be uniformly flushed through all capillaries 1 so that every active substance component can come into contact with every target molecule species (FIG. 3).

In the preferred embodiment, for mounting purposes the capillary plate 4 is laid on the lower part of the incubation table 16. In that case the edge regions 5 of the capillary plate come to lie on a soft seal 17. Then spacers 18 are laid around the capillary plate 4, the upper part of the incubation table 19 is fitted on and pressure is applied by a clamp 20 by means of pressure springs 21 to the capillary plate 4 and the spacer 18 or the lower part of the incubation table 16, so that the seals 17 in the upper and lower parts of the incubation table 19 and 16 are compressed and seal off the capillary plate 4 towards the side. Then an ultrasonic transmitter 22 is pushed into an opening in the spacer 18 until it is in contact with the edge region 5 of the capillary plate 4.

To charge the device the piston 23 is pushed downwardly and the cavity which is formed by retraction of the piston 23 beneath the capillary plate 4 is filled with the desired active substance solution or suspension through the filling connection 24. The volume of the active substance solution or suspension should be at least 1.5 times the internal volume of the capillary plate 4 plus the volume of the cavity 25 above the capillary plate 4.

For incubation purposes when the discharge 26 and the filling connection 24 are closed the piston 23 is moved slowly upwardly so that the air can escape from the capillaries 1 into the cavity 25. Air which is still enclosed in capillaries 1 can be removed by acoustic irradiation with the ultrasonic transmitter 22. When the piston 23 is moved to the capillary plate 4 the cavity 25 is completely filled with active solution or suspension and both the air and also the superfluous active substance solution or suspension escape through lateral passages 27 into the compensating vessels 28. The solution or suspension in the capillaries 1 is then mixed with the solution or suspension in the cavity 25 by repeated upward and downward movement of the piston 23 with a short stroke and air bubbles still present in the cavity 25 are displaced stepwise into the compensating vessels 28.

To empty the device the piston 23 is pushed back to such an extent that the discharge 26 is cleared, through which the active substance solution or suspension is then removed by applying reduced pressure.

Washing of the device is effected in a similar manner using suitable washing solutions.

Positionally resolved detection of the active substance reaction with the target molecules can also take place in the device as the cavity 25 above the capillary plate 4 is delimited upwardly by a transparent window 29 and thus for example binding or cleavage of fluorophores in the device can be detected or tracked by means of the measuring device described with reference to FIG. 4.

Device for Detecting the Binding of Active Substances to Target Molecules

Detection methods for the binding of molecules are described in many different forms in the literature and in patents, being based mostly on the use of radioactive or optical markers. Optical methods which permit penetration of the branches or webs between the capillaries are used for detecting bindings in the capillary plate. The most varied optical methods are based on fluorescence markings (for example M V Rogers (1997), Light on high-throughput screening: fluorescence-based assay technologies, Drug discovery Today 2:156-160). Fluorescence marking is produced by coupling a fluorophore either to the target molecules or to the active substances. For reading-out purposes, in the preferred embodiment the individual sample volume which corresponds to the sample area 3 over the entire thickness of the capillary plate is completely penetrated by excitation light and also completely detected by the detection optics. In order to prevent cross-talk of adjacent sample areas, only one sample location is illuminated at a moment in time and detection is limited only to one sample location. The multiplicity of sample locations are detected by time-sequential rastering.

Measurement at a sample location can be effected both continuously and also with repetitive pulses. In the former case, irradiation is effected with a continuously radiating, band pass-filtered light source or a laser, wherein the narrow-band excitation light is adapted to the absorption of the fluorescence marker. Detection is effected in a narrow-band mode in the range of fluorescence emission of the fluorescence marker with a suitable photodetector. In the case of pulsed fluorescence excitation as shown in FIG. 4, a laser 30 is used for illumination purposes, the pulse duration of which is at least a third of the life of the marking fluorophore. The collimated beam of the laser 31 is reflected by a wavelength-selective beam splitter 32 in a direction towards the capillary plate 4. The beam is focussed by an objective lens 33 on to a sample area 3 of the capillary plate 4 in such a way that the radiation passes through the entire sample volume of a sample area 3. The isotropically radiated fluorescence light 34 of the fluorescence marking is collimated by the same objective lens 33 and passes through the selective beam splitter 32 by virtue of the greater wavelength of the fluorescence. Stray light of the excitation laser is greatly suppressed by a narrow-band filter 35, but the fluorescence light is passed at the highest possible transmission. The fluorescence light is focussed on to the photodetector 37 by a further objective lens 36. Time-resolved detection with a rise time of less than a third of the fluorescence life of the fluorophore means that the fluorescence signal can particularly advantageously be detected in a time gate integration procedure with a boxcar integrator 38 after decay both of the elastic stray light and also Raman-scattered light. The time gate is correspondingly opened approximately after double the laser pulse duration and remains open for approximately double the fluorophore life.

A trigger signal from the laser 39 supplies the time base for the time gate. Standardisation of the fluorescence light and thus correction in respect of fluctuations in the laser pulse energy can be implemented, by way of a second channel of the boxcar integrator 38, by means of a signal from the laser 40, which is proportional to the laser pulse energy. All data are collected in a computer 41 and finally plotting of the fluorescence intensity over the respective sample location can be represented and association of the detected signals with the target molecules can be effected.

Figure 1:
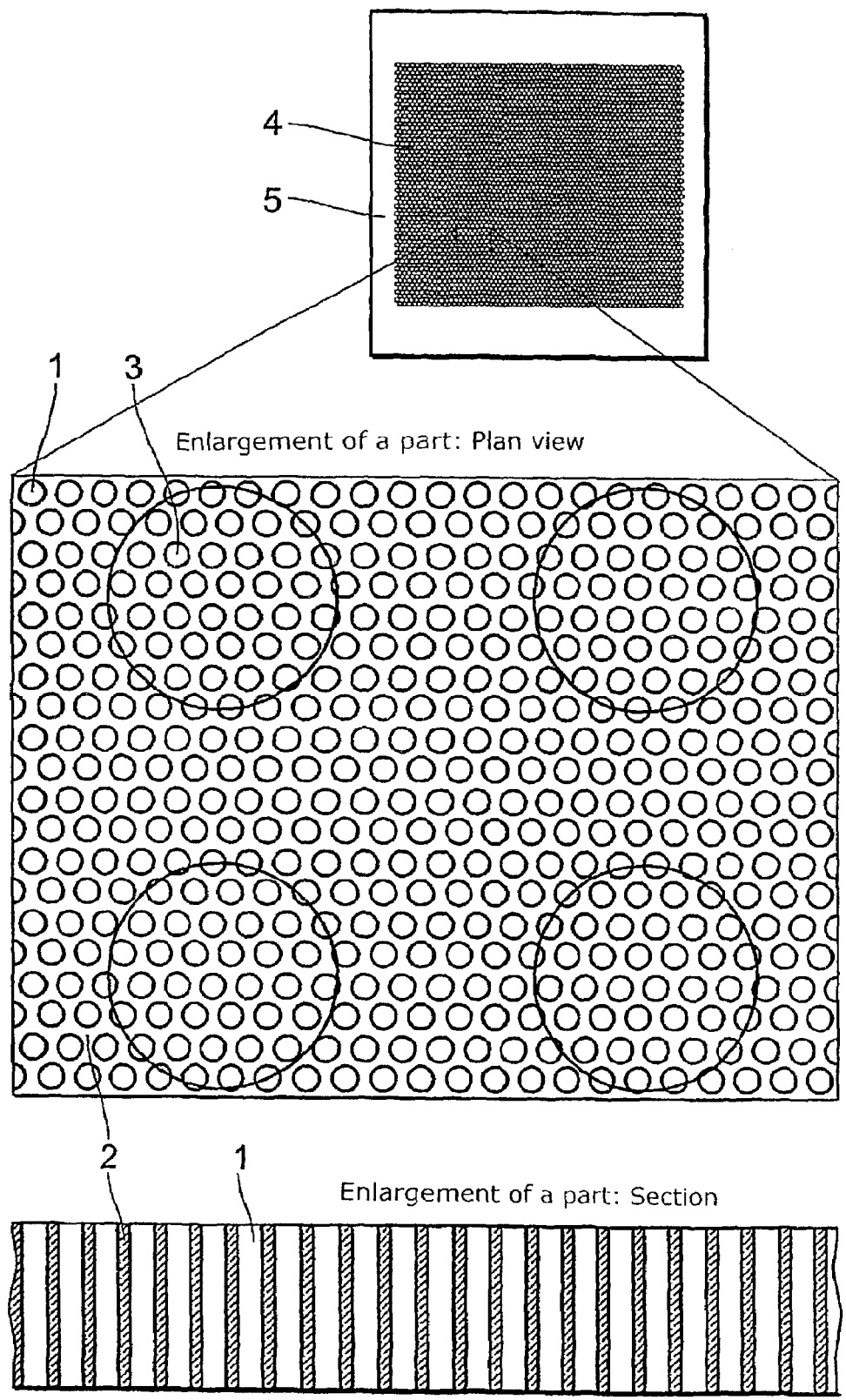
FIG. 1 is a diagrammatic view of a capillary plate 4 in plan and as a cross-section. The individual capillaries 1 are separated from each other by branch or web regions 2. The sample areas 3 include a plurality of capillary openings. The edge region of the plate 5 does not have any capillaries.
Figure 2:
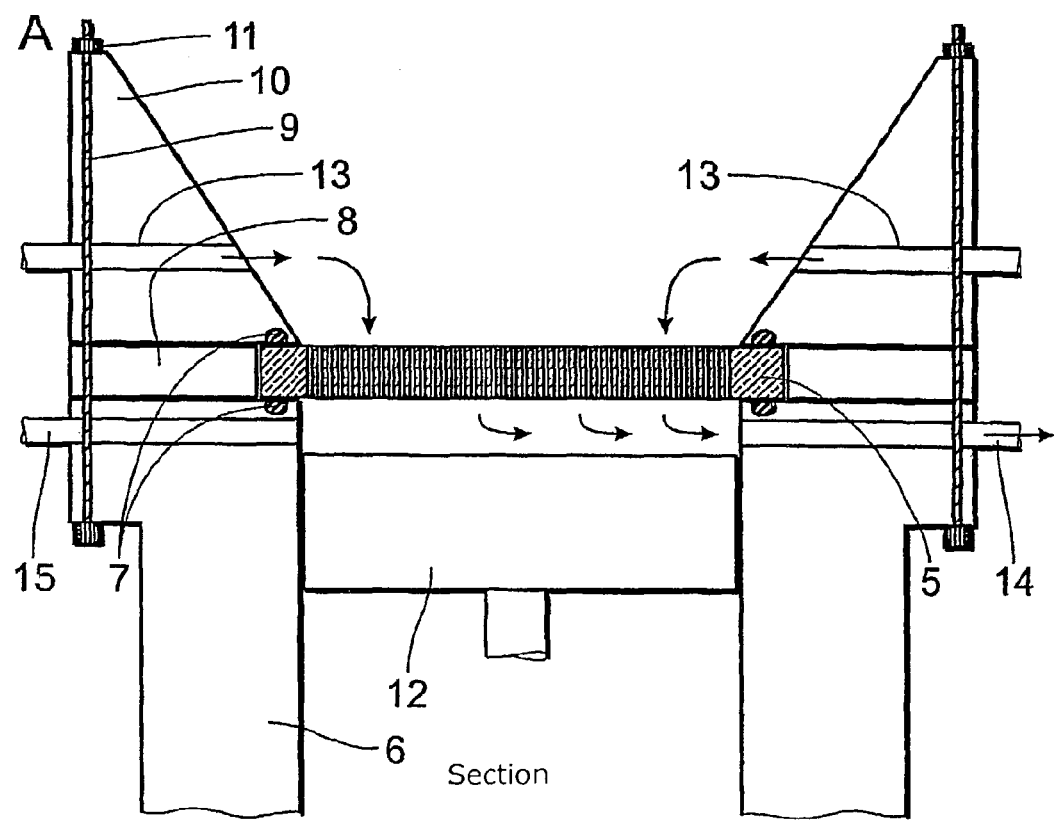
FIG. 2 shows a device for fully automatically washing, saturating and removing protection from the capillary plate 4 during synthesis of the substance library. In this case the capillary plate 4 is fitted between the upper part 10 and the lower part 6 of the synthesis table and fixed in position by means of suitable seals 7 and spacers 8 by way of a screwthreaded bolt 9 with nut 11. Washing solution feed flow means 13 are provided in the upper part 10 of the synthesis table and a reagent feed flow means 15 and a discharge 14 are provided in the lower part 6. A piston 12 can be moved in the lower part 6 of the synthesis table and can be moved to the underside of the capillary plate 4.
Figure 2:
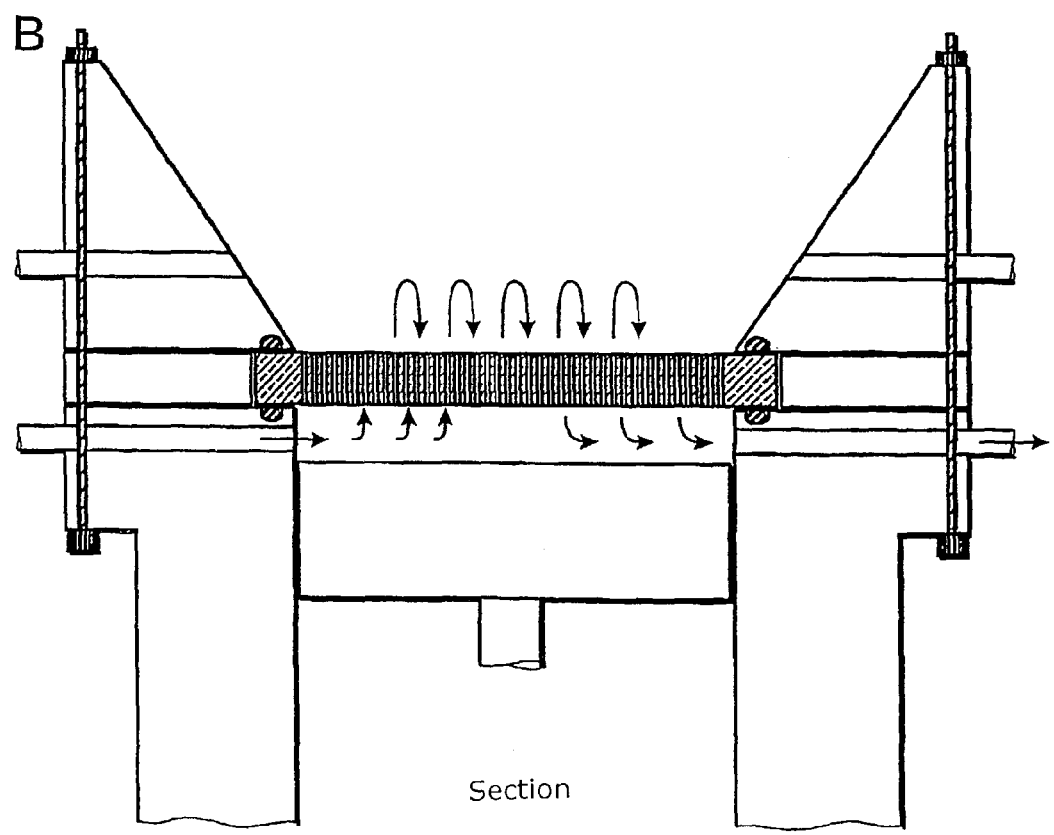
Figure 3:
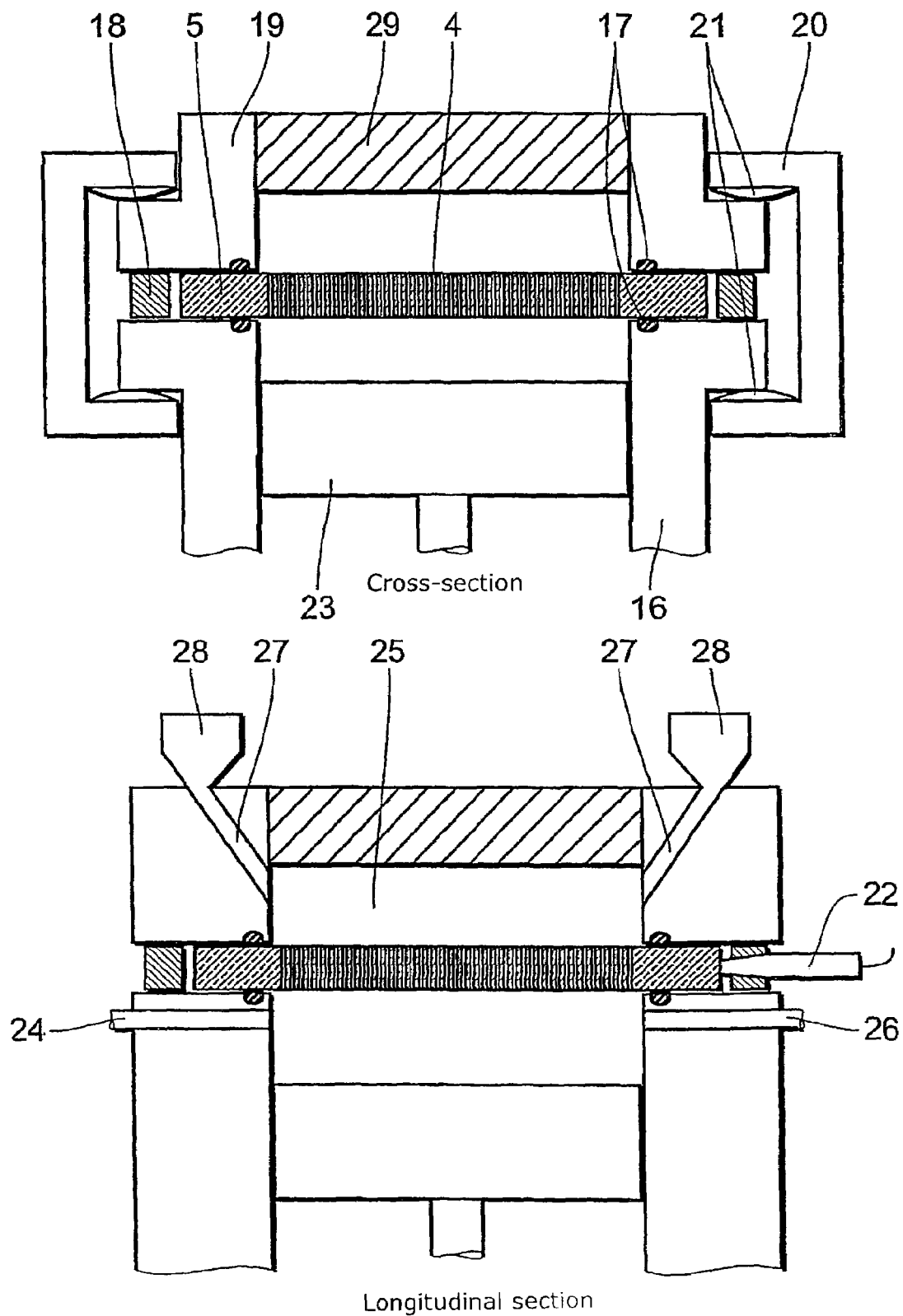
FIG. 3 shows a device for binding active substances to the substance library which is immobilised on the capillary plate. The capillary plate 4 is fitted between the upper part 19 and the lower part 16 of the incubation table and fixed in position by means of suitable seals 17 and spacers 18 by a clamp 20 with a pressure spring 21. An ultrasonic transmitter 22 is mounted laterally to the capillary plate 4. Disposed in the lower part of the incubation table are a filling connection 24 and a discharge 26 for the active substance solutions which can be pressed with a piston 23 through the capillary plate 4 into the upper cavity 25. Lateral passages 27 lead from the cavity 25 into a compensating vessel which serves to catch displaced air and excess active substance solution. The cavity 25 is closed off at its top by a transparent window 29 so that direct optical detection of reactions in the device is possible.
Figure 4:
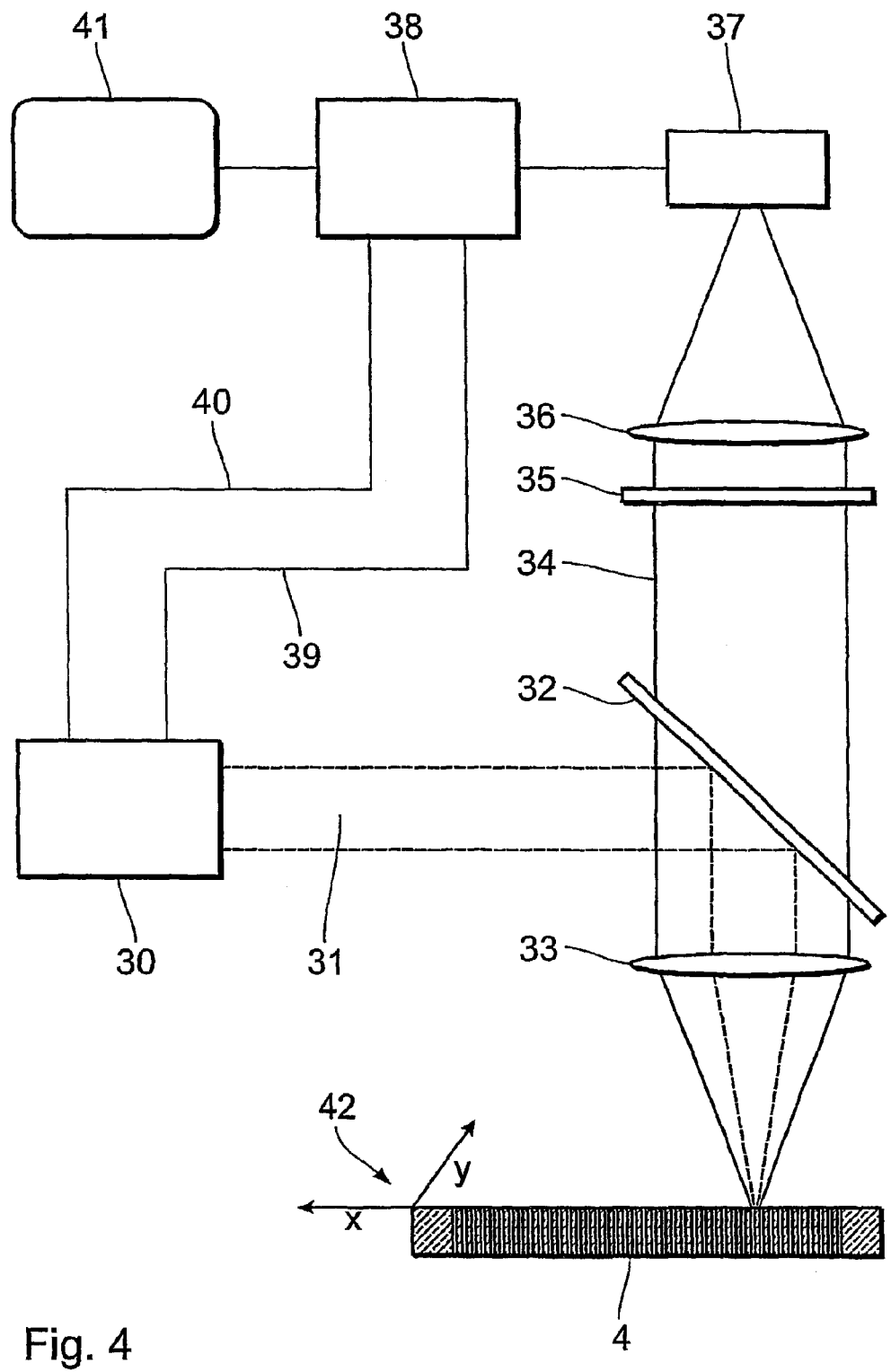
FIG. 4 is a diagrammatic view of a device for detecting the binding of active substances to the substance library by means of optical methods. Fluorophore-marked target molecules on the capillary plate 4 are excited to fluorescence by a laser beam 31 which is produced by a pulsed diode laser 30 and which is deflected on to the sample area by a wavelength-selective beam splitter 32 and an objective lens 33. The radiated fluorescence light 34 passes through the beam splitter 32, a band pass filter 35 and a further objective lens 36 before it impinges on the photodetector 37. For integration of the fluorescence signal within a time gate, a boxcar integrator 38 receives a time trigger signal 39 from the laser and a signal 40 proportional to the laser energy for standardisation of the fluorescence signal. A movable sample table 42 is so controlled by a computer 41 that the sample areas can be successively measured. The standardised fluorescence signal is represented over the sample location.

LEGEND 1 capillary
2 branch region between capillaries
3 sample area
4 capillary plate
5 edge region of the capillary plate
6 lower part of the synthesis table
7 solvent-resistant seal
8 spacer
9 screwthreaded pin
10 upper part of the synthesis table
11 nut
12 piston
13 washing solution feed flow means
14 discharge
15 reagent feed flow means
16 lower part of the incubation table
17 seal
18 spacer
19 upper part of the incubation table
20 clamp
21 pressure spring
22 ultrasonic transmitter
23 piston
24 filling connection
25 cavity
26 discharge
27 passage
28 compensating vessel
29 transparent window
30 pulsed diode laser
31 laser beam
32 beam splitter
33 objective lens
34 radiated fluorescence light
35 band pass filter
36 objective lens
37 photodetector 38 boxcar integrator
39 trigger pulse from the laser
40 signal from the laser which is proportional to the laser pulse energy
41 computer
42 movable sample table Some preferred configurations of the arrangement according to the invention and the method according to the invention will also be set forth hereinafter.

A. Method and device for investigating the molecular interaction of soluble or suspendable active substances with solid-phase bonded peptidic or peptoid target molecules characterised in that the surface necessary therefor is provided within a plate in the form of capillaries. The capillaries pass through from one side of the plate to the opposite side but in so doing are not connected to each other.

B. A method and device as defined in A which are characterised in that a plurality of parallel capillaries are arranged in the plate, which draw liquids through capillary force into the capillaries and hold same therein.

C. A method and device as defined in the preceding paragraphs which are characterised in that the capillary plate is made from one of the materials glass, quartz, silicon, plastic material, semi-metal, ceramic, metal or a combination of said materials.

D. A method and device as defined in the preceding paragraphs which are characterised in that the internal surface is enabled for covalent bonding of target molecules or synthesis of the target molecules is effected.

E. A method and device as defined in the preceding paragraphs which are characterised in that the internal surface is covered by an organosilane layer which has functional groups for anchoring peptidic or peptoid target molecules.

F. A method and device as defined in the preceding paragraphs which are characterised in that γ-aminopropyltrialkoxysilane or other organofunctional silanes are used for the silanisation step.

G. A method and device as defined in the preceding paragraphs which are characterised in that when using metal or semi-metal capillary plates prior to the silanisation step an oxide layer is provided for binding the silane by means of surface oxidation of the capillary plate.

H. A method and device as defined in the preceding paragraphs which are characterised in that locally delimited sample areas are applied in the capillary plate.

I. A method and device as defined in the preceding paragraphs which are characterised in that a plurality of sample areas each of a diameter of up to 2000 μm or a number of up to 4000 adjacent capillaries are applied on a capillary plate.

J. A method and device as defined in the preceding paragraphs which are characterised in that the capillaries are of a length and the capillary plate is of a thickness of between 100 and 2000 μm.

K. A method and device as defined in the preceding paragraphs which are characterised in that the functional group of the organosilane layer is temporarily protected by pipetting a substance on to the capillary plate. The region protected in that way represents a sample area.

L. A method and device as defined in the preceding paragraphs which are characterised in that a protected anchor molecule is produced at each binding location of the sample area by pipetting a reagent on to the capillary plate, wherein the anchor molecule serves at the same time as a spacer in relation to the internal surface.

M. A method and device as defined in the preceding paragraphs which are characterised in that a protected sample area is applied by pipetting on to the plate fluorenylmethoxycarbonyl (FMOC)-protected α-aminopoly(ethyleneglycol)-ω-propionic acid-N-hydroxybenzotriazole ester.

N. A method and device as defined in the preceding paragraphs which are characterised in that all non-protected regions of the capillary plate are chemically saturated.

O. A method and device as defined in the preceding paragraphs which are characterised in that the protective groups are removed in the sample areas of the entire capillary plate.

P. A method and device as defined in the preceding paragraphs which are characterised in that peptides or peptoid target molecules are positionally dependently sequentially synthesised out of amino acids in the sample areas of the capillary plate.

Q. A method and device as defined in the preceding paragraphs which are characterised in that the complete peptide or peptoid target molecules are bonded in positionally dependent manner in the sample areas of the capillary plate.

R. A method and device as defined in the preceding paragraphs which are characterised in that a substance library is built up by the positionally dependently different sequences of peptide or peptoid target molecules.

S. A method and device as defined in the preceding paragraphs which are characterised in that a closed and variable volume provided with a valve exists on at least one side of the capillary plate, into which volume liquids with soluble or suspendable active substances and other liquids and gases can be introduced and sucked away.

T. A method and device as defined in the preceding paragraphs which are characterised in that gas bubbles can be dissolved by coupling ultrasound to the capillary plate.

U. A method and device as defined in the preceding paragraphs which are characterised in that the reaction speeds in the capillaries are increased by coupling ultrasound.

V. A method and device as defined in the preceding paragraphs which are characterised in that the binding of the active substances to the target molecules is detected.

W. A method and device as defined in the preceding paragraphs which are characterised in that a change in the target molecules can be produced by the active substances and detected.

X. A method and device as defined in the preceding paragraphs which are characterised in that the capillary plate is transparent or optical and is freely accessible to optical measurement.

Y. A method and device as defined in the preceding paragraphs which are characterised in that soluble or suspendable active substances are fluorescence-marked and introduced into the capillaries.

Z. A method and device as defined in the preceding paragraphs which are characterised in that after a given time the non-bonded active substances are removed and the bonded active substances are detected on the basis of fluorescence marking.

AA. A method and device as defined in the preceding paragraphs which are characterised in that the solid-phase bonded peptidic or peptoid target molecules are fluorescence-marked.

BB. A method and device as defined in the preceding paragraphs which are characterised in that soluble or suspendable active substances, acids or other liquids are flushed into the capillaries, flushed out again after a given time, and the presence of the still bonded fluorescence-marked target molecules is detected.

CC. A method and device as defined in the preceding paragraphs which are characterised in that the fluorescence marking is excited and detected with light in the UV, in the visible range or near infrared.

DD. A method and device as defined in the preceding paragraphs which are characterised in that fluorescence excitation is effected with a pulsed diode laser with a pulse duration of less than 10 ns.

EE. A method and device as defined in the preceding paragraphs which are characterised in that detection of fluorescence is effected for the suppression of stray light in a time gate after decay of the excitation pulse.

What is claimed is:

1. A method of preparing a substance library for investigating the molecular interaction of soluble or suspendable substances with solid-phase bounded peptidic or peptoid target molecules wherein the substance library comprises a plurality of parallel capillaries arranged in a plate, the method comprising the following steps:
   a) applying an organosilane layer on an internal surface of the capillaries, said organosilane layer having functional groups for anchoring peptidic or peptoid target molecules;
   b) defining sample areas wherein each sample areas comprises a plurality of adjacent capillaries, and wherein defining said sample areas is performed by position dependent application of a protecting substance temporarily protecting the functional groups of the organosilane layer of the capillaries within said sample areas or by position-dependent application of a protected anchor molecule within said sample areas;
   c) saturating the capillaries in the plate outside the sample areas with a deactivation reagent such that neither synthesis nor coupling of target molecules can occur in the capillaries outside the sample areas;
   d) deprotecting all protected functional groups or anchor molecules in the sample areas; and
   e) synthesizing peptidic or peptoid target molecules in the sample areas by pipetting solutions into the capillaries of the sample areas; wherein said solutions contain amino acids for sequential synthesis of peptide or peptoid target molecules or wherein said solutions are coupling solutions for coupling complete peptide or peptoid target molecules.

2. The method of claim 1, wherein a protected $\alpha$-aminopoly(ethyleneglycol)-$\omega$-carboxylic acid active ester is used as the protected anchor molecule in step b).

3. The method of claim 2, wherein fluorenylmethoxycarbonyl (FMOC)-protected $\alpha$-aminopoly(ethyleneglycol)-$\omega$-propionic acid-N-hydroxybenzotriazole ester is used as the protected anchor molecule in step b).

4. The method of claim 1, wherein the capillary plate comprises metal or semi-metal, and wherein prior to applying an organosilane layer according to step a), an oxide layer is provided for binding the silane by means of surface oxidation of the internal surface of the capillaries.

5. The method of claim 1, wherein a plurality of sample areas are each of a diameter of up to 2,000 μm.

6. The method of claim 1, wherein the capillaries are of a length and the capillary plate is of a thickness of between 100 and 2,000 μm.

7. The method of claim 1, wherein up to 4,000 adjacent capillaries are present in a sample area.

* * * * *

UNITED STATES PATENT AND TRADEMARK OFFICE
CERTIFICATE OF CORRECTION

PATENT NO.         : 7,431,685 B2
APPLICATION NO.    : 10/239986
DATED              : October 7, 2008
INVENTOR(S)        : Andreas Frey et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 655 days Delete the phrase "by 655 days" and insert -- by 797 days --

Signed and Sealed this

Twentieth Day of October, 2009

David J. Kappos
*Director of the United States Patent and Trademark Office*